(12) United States Patent
Gajendra et al.

(10) Patent No.: US 12,415,210 B2
(45) Date of Patent: Sep. 16, 2025

(54) AUTO-CLEANING OF SMART AIR IONIZER

(71) Applicant: B/E AEROSPACE, INC., Winston Salem, NC (US)

(72) Inventors: Hemanth Raghav Gajendra, Bangalore (IN); Sujan Jayasimha Vasishta, Bangalore (IN); Skandan Berikai Kuppan, Bangalore (IN); Sai Sankalp Shekar, Bengaluru (IN)

(73) Assignee: B/E AEROSPACE, INC., Winston Salem (NC)

( * ) Notice: Subject to any disclaimer, the term of this patent is extended or adjusted under 35 U.S.C. 154(b) by 222 days.

(21) Appl. No.: 18/343,654

(22) Filed: Jun. 28, 2023

(65) Prior Publication Data
US 2024/0351075 A1   Oct. 24, 2024

(30) Foreign Application Priority Data
Apr. 24, 2023   (IN) .............................. 202341029410

(51) Int. Cl.
| | | |
|---|---|---|
| H05F 3/00 | (2006.01) |
| A61L 9/22 | (2006.01) |
| B08B 7/02 | (2006.01) |
| B08B 13/00 | (2006.01) |
| B64D 13/06 | (2006.01) |

(52) U.S. Cl.
CPC *B08B 7/02* (2013.01); *A61L 9/22* (2013.01); *B08B 13/00* (2013.01); *B64D 13/06* (2013.01); *A61L 2209/111* (2013.01); *B64D 2013/067* (2013.01)

(58) Field of Classification Search
None
See application file for complete search history.

(56) References Cited

U.S. PATENT DOCUMENTS

| | | | | |
|---|---|---|---|---|
| 3,874,858 A | * | 4/1975 | Klugman | B03C 3/16 96/290 |
| 4,057,405 A | * | 11/1977 | Cheney | B03C 3/766 55/300 |
| 4,353,718 A | | 10/1982 | Franzen et al. | |
| 7,252,701 B2 | | 8/2007 | Tolvanen | |
| 9,925,567 B2 | | 3/2018 | Waddell | |

(Continued)

FOREIGN PATENT DOCUMENTS

| | | |
|---|---|---|
| CN | 204254745 | 4/2015 |
| EP | 397208 | 7/1994 |

(Continued)

OTHER PUBLICATIONS

European Patent Office, European Search Report dated Aug. 1, 2024 in Application No. 24171820.4.

Primary Examiner — Stephen W Jackson
(74) Attorney, Agent, or Firm — SNELL & WILMER L.L.P.

(57) ABSTRACT

A cleaning mechanism for a smart air ionizer is provided. The cleaning mechanism includes an electrode configured with a plurality of carbon bristles exposed to an airflow and configured to ionize air in the airflow via the plurality of carbon bristles, a vibration mechanism, and a controller circuit coupled to the vibration mechanism, the controller circuit including a controller configured to operate the vibration mechanism to clean the plurality of carbon bristles.

19 Claims, 9 Drawing Sheets

(56) References Cited

U.S. PATENT DOCUMENTS

2015/0236484 A1* 8/2015 Chen .................. H01T 19/04
       361/231
2017/0169986 A1* 6/2017 Gefter .................. H01J 37/026
2019/0125919 A1 5/2019 Ellis et al.

FOREIGN PATENT DOCUMENTS

JP  2016100083  5/2016
WO 2021213078 10/2021

* cited by examiner

AUTO-CLEANING OF SMART AIR IONIZER

CROSS-REFERENCE TO RELATED APPLICATIONS

This application claims priority to, and the benefit of, India Provisional Patent Application No. 202341029410, filed Apr. 24, 2023 (DAS Code 4AB2) and titled "AUTO-CLEANING OF SMART AIR IONIZER," which is incorporated by reference herein in its entirety for all purposes.

FIELD

The present disclosure generally relates to systems for managing air quality in an aircraft, and more specifically, to automatically cleaning air ionizers in an aircraft.

BACKGROUND

Travel within aircraft includes the recirculation of air within the aircraft. Circulation of air within an enclosed space, such as aircraft, may include circulation of harmful pathogens (e.g., viruses, bacteria, etc.) and undesirable odors. Currently, commercial aircraft use air filters, including high efficiency particulate air (HEPA) filters, to filter the air during recirculation. Generally, air filters are placed at central locations and therefore may not have continuous effectiveness within the enclosed space. Furthermore, more effective air filters, such as HEPA filters, come with an increased cost both in terms of the filter itself as well as the energy used to force air through the air filter. Furthermore, air filters, including HEPA filters, do not remove odors from the air within the enclosed space.

SUMMARY

A cleaning mechanism for a smart air ionizer is disclosed herein. The cleaning mechanism includes an electrode configured with a plurality of carbon bristles exposed to an airflow and configured to ionize air in the airflow via the plurality of carbon bristles; a vibration mechanism; and a controller circuit coupled to the vibration mechanism, the controller circuit including a controller configured to operate the vibration mechanism to clean the plurality of carbon bristles.

In various embodiments, the cleaning mechanism further includes an ion probe connected to the controller. In various embodiments, the controller is configured to receive a detected ion count from the ion probe and operate the vibration mechanism based on the detected ion count.

In various embodiments, the controller operates the vibration mechanism based on a predetermined ion threshold. In various embodiments, the controller sends command to the vibration mechanism to clean the plurality of carbon bristles in response to at least one of the detected ion count failing to meet the predetermined ion threshold or the detected ion count failing to exceed the predetermined ion threshold.

In various embodiments, the vibration mechanism is coupled to the electrode. In various embodiments, the vibration mechanism cleans the plurality of carbon bristles through vibrating the electrode. In various embodiments, the vibration mechanism vibrates the electrode at a predetermined frequency. In various embodiments, the vibration mechanism is at least one of an eccentric rotating mass (ERM) motor or a printed circuit board (PCB) motor. In various embodiments, cleaning the plurality of carbon bristles ejects particulates that have accumulated on the plurality of carbon bristles.

Also disclosed herein is a passenger service unit for use above an airline seat. The passenger service unit includes a body, an air outlet mounted to the body, an electrode mounted adjacent the air outlet, the electrode configured with a plurality of carbon bristles exposed to an airflow to ionize air in the airflow, a vibration mechanism, an air ionizer circuit connected to the electrode, a processor coupled to the air ionizer circuit, and a memory operatively coupled to the processor, In various embodiments, the memory includes instructions stored thereon that, when executed by the processor, cause the processor to: receive a detected ion count from an ion probe, determine whether the detected ion count meets or exceeds a predetermined ion threshold, and, responsive to at least one of detected the ion count failing to meet the predetermined ion threshold or the detected ion count failing to exceed the predetermined ion threshold, send a command to the vibration mechanism to clean the plurality of carbon bristles.

In various embodiments, the vibration mechanism is coupled to the electrode. In various embodiments, the vibration mechanism cleans the plurality of carbon bristles through vibrating the electrode. In various embodiments, the vibration mechanism vibrates the electrode at a predetermined frequency. In various embodiments, the vibration mechanism is at least one of an eccentric rotating mass (ERM) motor or a printed circuit board (PCB) motor. In various embodiments, cleaning the plurality of carbon bristles ejects particulates that have accumulated on the plurality of carbon bristles.

Additionally disclosed herein is a method for controlling an air ionizer. The method includes receiving, by a processor, a detected ion count from a probe, the detected ion count being representative of ions produced by an electrode; comparing, by the processor, the detected ion count to a predetermined ion threshold; and, responsive to the detected ion count being below the predetermined ion threshold, sending, by the processor, a command to a vibration mechanism to clean a plurality of carbon bristles coupled to the electrode.

In various embodiments, the vibration mechanism cleans the plurality of carbon bristles through vibrating the electrode. In various embodiments, the vibration mechanism vibrates the electrode at a predetermined frequency. In various embodiments, the vibration mechanism is at least one of an eccentric rotating mass (ERM) motor or a printed circuit board (PCB) motor. In various embodiments, cleaning the plurality of carbon bristles ejects particulates that have accumulated on the plurality of carbon bristles.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1:
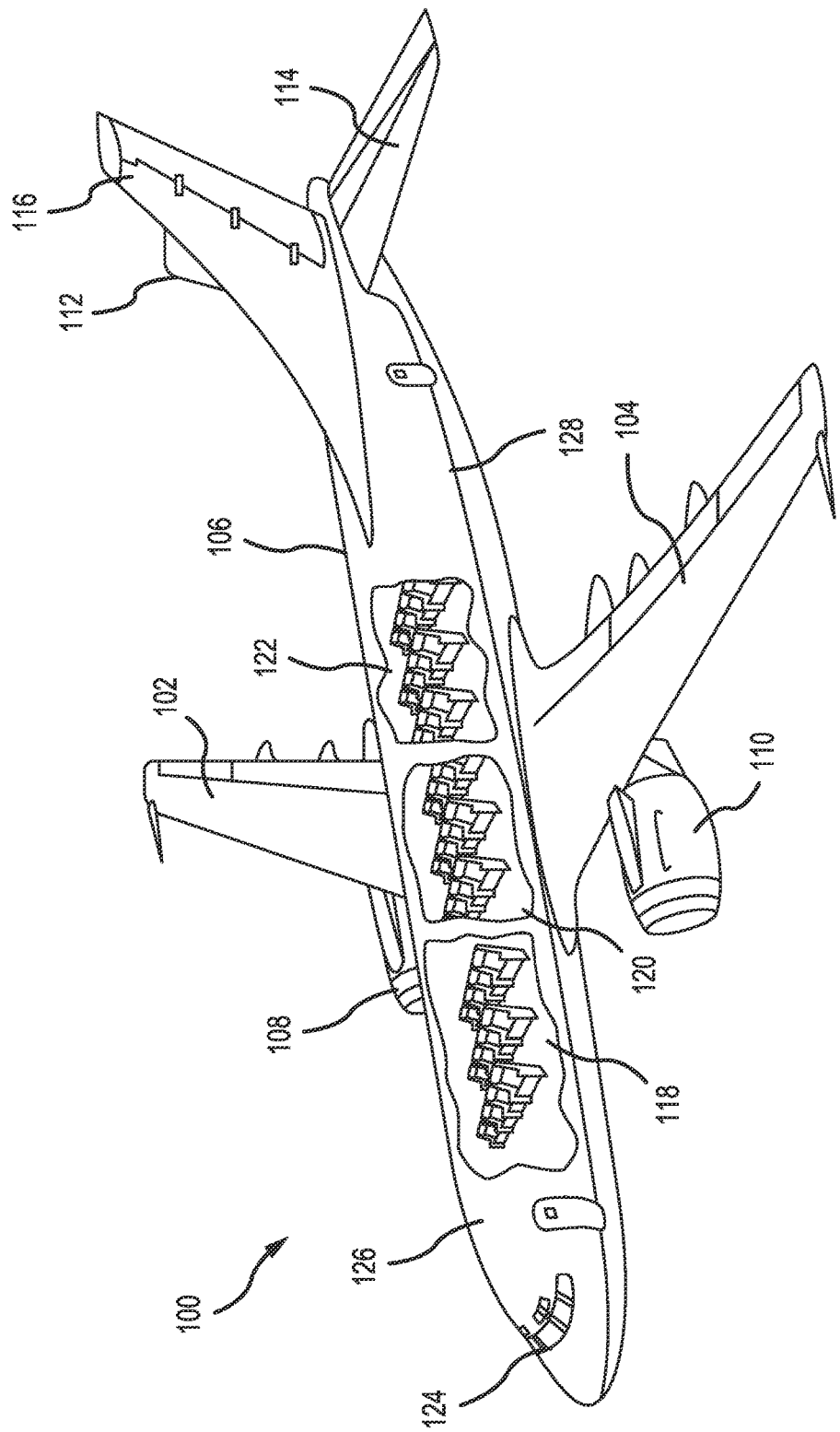
FIG. 1 illustrates an aircraft and various sections within the aircraft, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Disclosed herein are mechanisms for auto-cleaning a smart air ionizer. In various embodiments, the smart air ionizer may have a dual capability of neutralizing pathogens (e.g., bacteria, viruses, molds, etc.) and neutralizing undesirable odors (e.g., volatile organics, sulfur-based compounds, etc.). In various embodiments, the smart air ionizer may be used alongside existing air filters. In various embodiments, a high efficiency particulate air (HEPA) filter for improved performance. In various embodiments, the combination of the smart air ionizer and the air filter may perform at a higher minimum efficiency reporting value (MERV) rating than the MERV rating of the air filter. Accordingly, a non-HEPA filter paired with the smart air ionizer may perform with a higher MERV value than a HEPA filter. In various embodiments, the smart air ionizer ionizes the surrounding air, generating positive and negative ions. The positive and negative ions combine with pathogens and odor molecules in the air and effectively neutralizes both.

In various embodiments, the ionization of the air is based on ion emitters, i.e. carbon brushes. In various embodiments, the carbon brushes are configured with a plurality of carbon bristles, with a structure of each carbon bristle causing the surrounding air to conduct electricity, i.e. a dielectric breakdown. In that regard, in various embodiments, a topology of the plurality of carbon bristles is critical to the generation of ions. In various embodiments, the plurality of carbon bristles, when in operation, are exposed to surrounding environment and attract particulates. In various embodiments, the sedimentation of such particulates on and/or in the plurality of carbon bristles affect the efficiency of ion emission of the plurality of carbon bristles. Typically, ions created by air ionizer, such as negative ions and positive ions, have an active life span of about 30 seconds to about 75 seconds. In that regard, in various embodiments, there is a need for efficient distribution in air space and, by increasing the reach of these ions, a large volume of air may be covered.

Accordingly, in various embodiments, mechanisms are provided for auto-cleaning a smart air ionizer. In various embodiments, a cleaning mechanism is coupled to each support electrode, i.e. each electrode assembly that supports its associated plurality of carbon brushes. In various embodiments, in operation, each cleaning mechanism is in physical contact with electrode assembly and vibrates at a predetermined frequency. In that regard, in various embodiments, each electrode assembly is free to move, i.e. are not constrained. Accordingly, in various embodiments, particulates that accumulate on the plurality of carbon bristles associated with the electrode assembly are ejected from the plurality of carbon bristles due to one or more of a vibratory force, an inertial force, and/or a fictional force.

Referring now to FIG. 1, an aircraft 100 and various sections within the aircraft is illustrated, in accordance with various embodiments. Aircraft 100 is an example of a passenger or transport vehicle in which smart air ionizers may be implemented in accordance with various embodiments. In various embodiments, aircraft 100 has a starboard wing 102 and a port wing 104 attached to a fuselage 106. In various embodiments, aircraft 100 also includes a starboard engine 108 connected to starboard wing 102 and a port engine 110 connected to port wing 104. In various embodiments, aircraft 100 also includes a starboard horizontal stabilizer 112, a port horizontal stabilizer 114, and a vertical stabilizer 116. In various embodiments, aircraft 100 also includes various cabin sections, including, for example, a first cabin section 118, a second cabin section 120, a third cabin section 122, and a pilot cabin 124. In various embodiments, aircraft 100 may include a front lavatory 126 and/or a rear lavatory 128.

Figure 2:
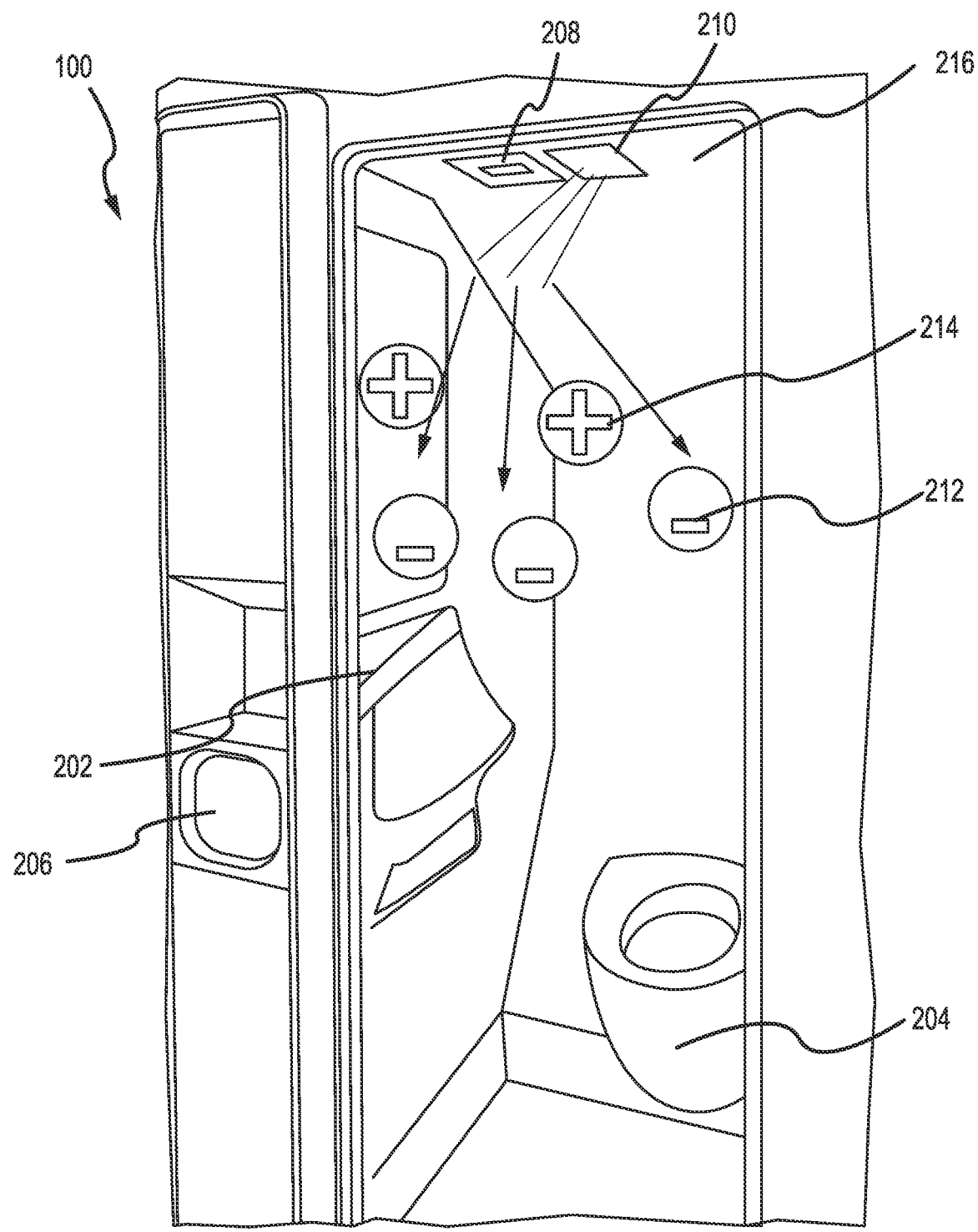
FIG. 2 illustrates a lavatory in an aircraft with a smart air ionizer, in accordance with various embodiments.

Referring now to FIG. 2, a lavatory 200 is illustrated, in accordance with various embodiments. In various embodiments, lavatory 200 may be an example of front lavatory 126 or rear lavatory 128. Lavatory 200 may include a sink 202, a toilet 204, a trash receptacle 206, an air vent 208, and an air ionizer 210. In various embodiments, air ionizer 210 may be mounted on ceiling 216 of lavatory 200, adjacent to air vent 208. In various embodiments, air ionizer 210 may be mounted within air vent 208. Air ionizer 210 generates ionized air particles, including negative ions 212 and positive ions 214, that are spread throughout lavatory 200 by air flow from air vent 208.

In various embodiments, air ionizer 210, and more specifically, ions created by air ionizer 210 may neutralize pathogens (e.g., bacteria, viruses, molds, dust, etc.) and/or malodor (i.e., unpleasant smells) that are airborne and on surfaces. Pathogens and malodor may be generated and/or spread by sink 202, toilet 204, and trash receptacle 206, among other locations. Pathogens and malodor may be airborne and/or settle on surfaces within lavatory 200, including sink 202, toilet 204, and trash receptacle 206, among others.

As illustrated in FIG. 2, air ionizer 210 may be placed adjacent to air vent 208 so that air ionizer 210 ionizes the air exiting the air vent 208. Generally, ions created by air ionizer 210 have an active life span of about 30 seconds to about 75 seconds, and more specifically, about 45 seconds to about 60 seconds. Accordingly, locating the air ionizer 210 adjacent to air vent 208 improves the efficacy of ions as compared to placing an air ionizer within ductwork of an air handling system or adjacent an air filter within the air handling system. In various embodiments, air ionizer 210 may be placed inside air vent 208, and more specifically, within the ductwork behind air vent 208 and immediately adjacent to air vent 208. In various embodiments, air ionizer 210 may be incorporated into air vent 208 so the air ionizer 210 and air vent 208 operate as a single unit to ionize and disperse air throughout lavatory 200.

Figure 3:
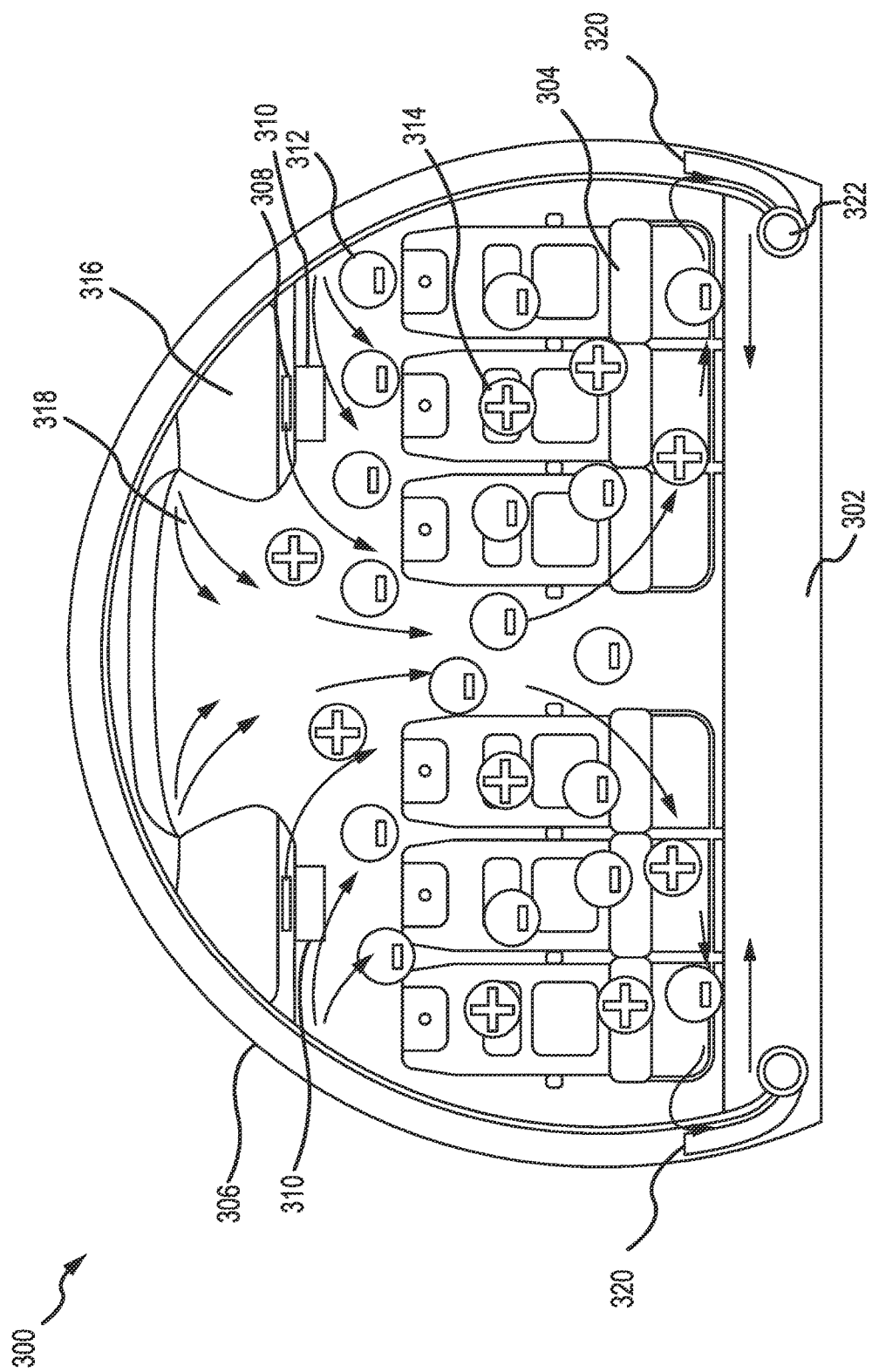
FIG. 3 illustrates a cabin area in an aircraft with a smart air ionizer system, in accordance with various embodiments.

Referring now to FIG. 3, a cabin 300 of an aircraft (e.g., aircraft 100) is illustrated, in accordance with various embodiments. Cabin 300 may be an example of first cabin section 118, second cabin section 120, and/or third cabin section 122. Cabin 300 includes a floor 302, one or more rows of passenger seats 304 mounted to floor 302, a fuselage 306 surrounding the cabin 300 to form outer walls and ceiling of cabin 300, and overhead bins 316 that are mounted to fuselage 306. Cabin 300 further includes passenger air outlets 308 are mounted underneath overhead bins 316 and above one or more of the passenger seats 304. In various embodiments, passenger air outlet 308 may be an air grasper that is commonly placed above the passenger seats 304 and is adjustable by rotating a nozzle on the air grasper. In various embodiments, there may be one passenger air outlet 308 for each passenger seat 304. Cabin 300 further includes cabin air outlets 318 that conduct, or provide, air from above overhead bins 316. Air in cabin 300 is circulated (as indicated by the arrows) from passenger air outlets 308 and cabin air outlets 318 throughout cabin 300, including over and around, passenger seats 304, and into one or more air returns 320. In various embodiments, air may circulate through air ducts 322 and through air filters before returning into cabin 300 through passenger air outlets 308 and cabin air outlets 318.

As illustrated in FIG. 3, air ionizer 310 is placed adjacent to the passenger air outlet 308 to ionize the air as it exits the passenger air outlet 308. In various embodiments, there may be one air ionizer 310 for each passenger air outlet 308. In various embodiments, there may be one air ionizer 310 for each row of the passenger seats 304, where each passenger seat 304 is associated with one passenger air outlet 308. In various embodiments, one or more air ionizers 310 may be placed adjacent to cabin air outlets 318. In various embodiments, air ionizer 310 may be placed inside air system ductwork adjacent to the passenger air outlet 308 and cabin air outlet 318. In various embodiments, air ionizer 310 may be incorporated into a passenger service unit (PSU) within cabin 300.

Figure 4B:
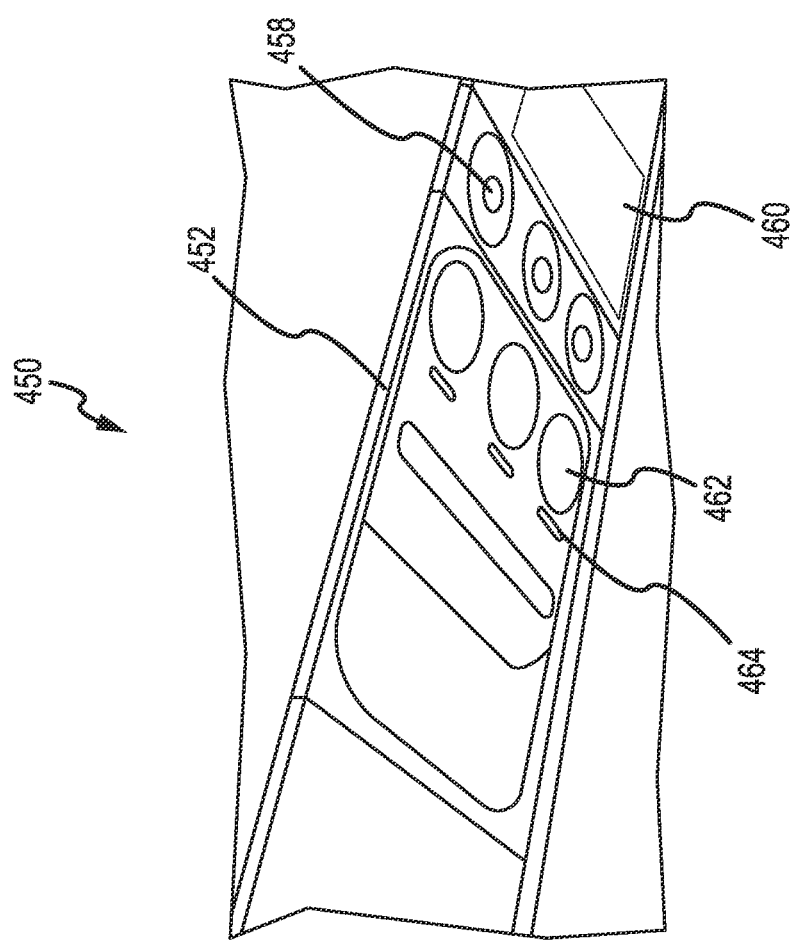
FIGS. 4A and 4B illustrate a smart ionizer install in an aircraft, in accordance with various embodiments.
Figure 4A:
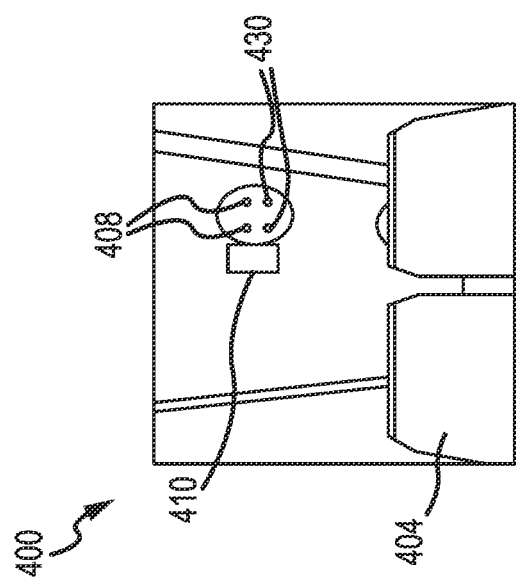

Referring now to FIGS. 4A and 4B, illustrated are a passenger service unit (PSU) 400 and PSU 450 that may be used in an aircraft cabin (e.g., cabin 300), in accordance with various embodiments. FIG. 4A illustrates PSU 400 above two passenger seats 404, PSU 400 including two passenger air outlets 408, an air ionizer 410, and two reading lights 430. As illustrated, air ionizer 410 is located on PSU 400 and adjacent to the two passenger air outlets 408. Placing the air ionizer 410 adjacent to the two passenger air outlets 408 improves the performance of air ionizer 410 by increasing the amount of time the ions created by air ionizer 410 are circulated through cabin 300. In various embodiments, air ionizer 410 may be located inside PSU 400 and adjacent to the two passenger air outlets 408. Placing the air ionizer 410 inside PSU 400 may be more visually appealing with little to no degradation in the performance of air ionizer 410. In various embodiments, PSU 400 may be installed above a two-seat aisle in an aircraft.

FIG. 4B illustrates PSU 450 including a body 452 that includes three passenger air outlets 458, an air ionizer 460, three passenger reading lights 462, and three call buttons 464. Air ionizer 460 is placed on an outside of the body 452 adjacent the three passenger air outlets 458 to provide improved ionizing performance. In various embodiments, air ionizer 460 may be placed on an inside of the body 452 and adjacent to the passenger air outlets 458 with little to no degradation in performance of air ionizer 410. In various embodiments, PSU 450 may be installed above a three-seat aisle in an aircraft.

Figure 5:
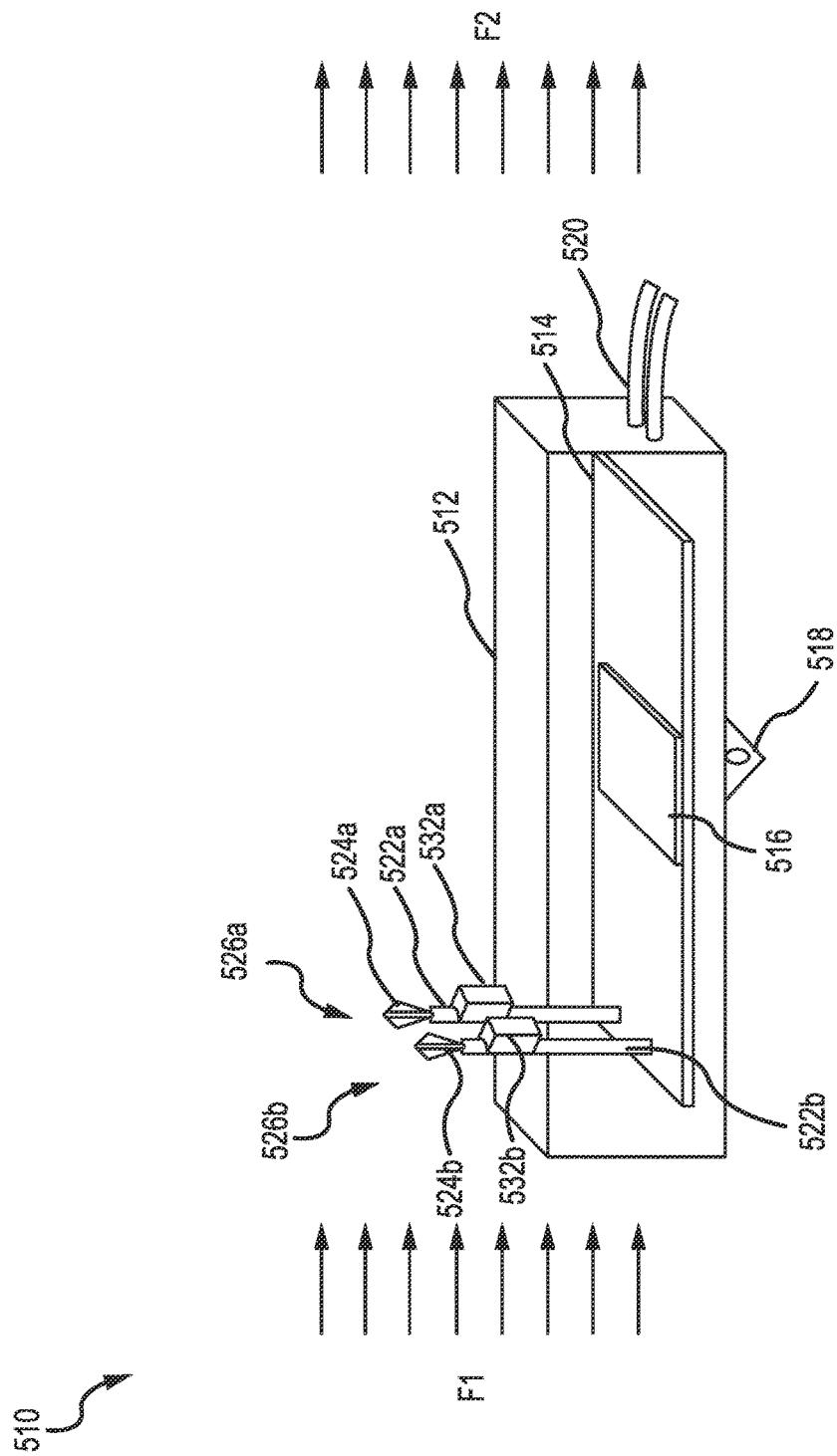
FIG. 5 illustrates a perspective view of a smart air ionizer unit, in accordance with various embodiments.

Referring now to FIG. 5, illustrated is a smart air ionizer 510, in accordance with various embodiments. Smart air ionizer 510 may be an example of air ionizer 210 described above with respect to FIG. 2, air ionizer 310 described above with respect to FIG. 3, air ionizer 410 described above with respect to FIG. 4A, or air ionizer 460 described above with respect to FIG. 4B. In various embodiments, smart air ionizer 510 includes an enclosure 512, an air ionizer circuit 514, a high voltage circuit 516, a mounting flange 518, and an input power cable 520. In various embodiments, high voltage circuit 516 is connected to air ionizer circuit 514 and both are disposed within enclosure 512. In various embodiments, enclosure 512 may be mounted to a ceiling (e.g., ceiling 216), a wall, a passenger service unit (e.g., PSU 400, PSU 450), or an air duct, among other locations. In various embodiments, mounting flange 518 may be used to secure enclosure 512 to the surface on which it is mounted.

In various embodiments, smart air ionizer 510 further includes a first high voltage wire 522a, a second high voltage wire 522b, a first carbon brush 524a, and a second carbon brush 524b. In various embodiments, first high voltage wire 522a is connected to air ionizer circuit 514 at a first end and to first carbon brush 524a at a second end. In various embodiments, first high voltage wire 522a and first carbon brush 524a may be collectively referred to as a first electrode 526a. In various embodiments, second high voltage wire 522b is connected to air ionizer circuit 514 at a first end and to second carbon brush 524b at a second end. In various embodiments, second high voltage wire 522b and second carbon brush 524b may be collectively referred to as a second electrode 526b. Also illustrated are an air flow F1 into smart air ionizer 510 and an ionized air flow F2 out smart air ionizer 510.

Input power cable 520 provides power for smart air ionizer 510. In various embodiments, input power cable 520 may provide electrical power, for example, 115 VAC. In various embodiments, input power cable 520 may provide 28 VDC. In various embodiments, another AC or DC voltage may be provided. Power provided by input power cable 520 may be used to power the air ionizer circuit 514 and high voltage circuit 516.

Air ionizer circuit 514 includes a controller that is configured to control the various features and elements of the smart air ionizer. Air ionizer circuit 514 may be configured for use with various external high voltage ranges and electrode types (e.g., first and second high voltage wires 522a, 522b and first and second carbon brushes 524a, 524b). The controller may include one or more processors configured to implement various logical operations in response to execution of instructions, for example, instructions stored on a non-transitory, tangible, computer-readable medium. The one or more processors can be a general-purpose processor, a microprocessor, a microcontroller, a digital signal processor (DSP), an application specific integrated circuit (ASIC), a field programmable gate array (FPGA) or other programmable logic device, discrete or transistor logic, discrete hardware components, or any combination thereof. The controller may further include memory to store data, executable instructions, system program instructions, and/or controller instructions to implement the control logic of the controller.

High voltage circuit 516 may include a switching regulator, a transformer, and a passive voltage tripler. In various embodiments, high voltage circuit 516 may receive input voltage from input power cable 520. In various embodiments, high voltage circuit 516 may output about 2.5 KV to about 12.5 KV, and more specifically, about 5 KV to about 10 KV. In various embodiments, the controller in air ionizer circuit 514 may control the high voltage circuit 516. In various embodiments, the controller in air ionizer circuit 514 may control the output voltage of high voltage circuit 516. In various embodiments, an output current of high voltage circuit 516 may be limited to microamps.

The high voltage output of high voltage circuit 516 is sent to first electrode 526a and second electrode 526b. That is, the high voltage is sent to first high voltage wire 522a and second high voltage wire 522b and subsequently to first carbon brush 524a and second carbon brush 524b, respectively. Together, first electrode 526a and second electrode 526b use the high voltage output of high voltage circuit 516 to ionize the air surrounding first carbon brush 524a and second carbon brush 524b, respectively. Air ionizer circuit 514, and more specifically, the controller of air ionizer circuit 514 controls the voltage and current sent to first and second electrodes 526a, 526b.

Figure 6B:
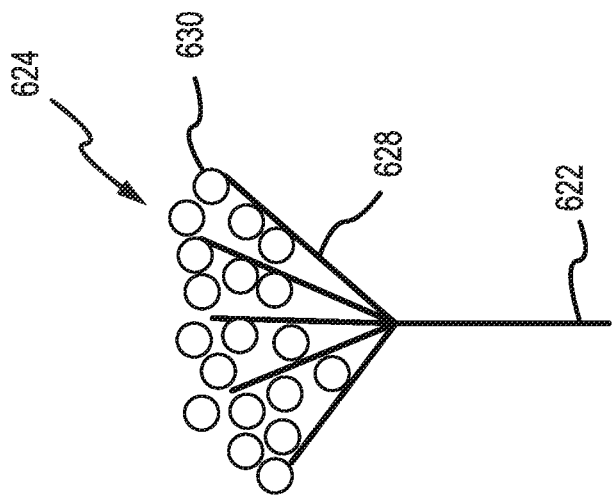
FIG. 6B illustrates an enlarged view of a plurality of carbon bristles with accumulated particulates, in accordance with various embodiments.
Figure 6A:
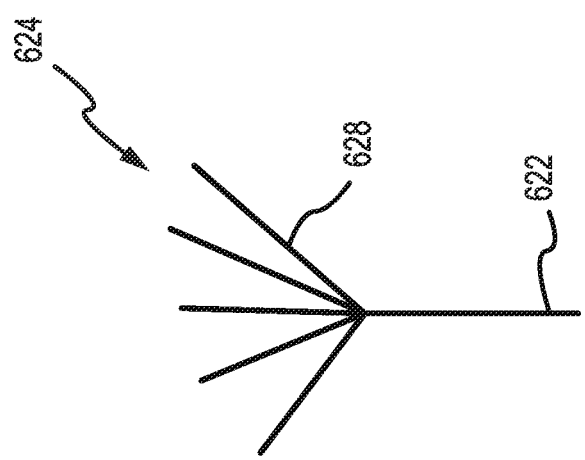
FIG. 6A illustrates an enlarged view of a carbon brush, in accordance with various embodiments.

With temporary reference to FIG. 6A, an enlarged view of a carbon brush, such as a first carbon brush 524a, and a second carbon brush 524b of FIG. 5, is illustrated in accordance with various embodiments. In various embodiments, carbon brush 624, which is coupled to high voltage wire 622, is a plurality of carbon bristles 628, with a structure of each carbon bristle causing the surrounding air to conduct electricity, i.e. a dielectric breakdown. In various embodiments, a topology of the plurality of carbon bristles 628 topology is important to the generation of ions. Accordingly, in various embodiments, the plurality of carbon bristles, when in operation, are exposed to surrounding environment and attract particulates. With temporary reference to FIG. 6B, an enlarged view of a plurality of carbon bristles with accumulated particulates is illustrated, in accordance with various embodiments. In various embodiments, when high voltage wire 622 is receiving power and the plurality of carbon bristles 628 are exposed to surrounding environment, particulates 630 accumulate on and/or in the plurality of carbon bristles, which affects the efficiency of ion emission of the plurality of carbon bristles 628.

In order to automatically clean the plurality of carbon bristles 628, in various embodiments, the controller in air ionizer circuit 514 may be configured to further control the first cleaning mechanism 532a and second cleaning mechanism 532b. In various embodiments, the first cleaning mechanism 532a and the second cleaning mechanism 532b may be a vibration mechanism. In various embodiments, the first cleaning mechanism 532a and the second cleaning mechanism 532b may be an eccentric rotating mass (ERM) motor or a printed circuit board (PCB) motor, among others. In various embodiments, the first cleaning mechanism 532a is coupled to and in physical contact with the first high voltage wire 522a and the second cleaning mechanism 532b is coupled to and in physical contact with second high voltage wire 522b. In various embodiments, the first cleaning mechanism 532a and the second cleaning mechanism 532b, under the control of the controller of the air ionizer circuit 514, are configured to vibrate at a predetermined frequency. In various embodiments, the controller of the air ionizer circuit 514 may be configured to turn the first cleaning mechanism 532a and the second cleaning mechanism 532b on or off based in input from an ion probe that detecting the number of ions produced by first and second electrodes 526a, 526b. In that regard, in various embodiments, responsive to the first cleaning mechanism 532a and the second cleaning mechanism 532b, along with their respective high voltage wires, i.e. the first high voltage wire 522a and second high voltage wire 522b, being activated by the controller of the air ionizer circuit 514, the first cleaning mechanism 532a and the second cleaning mechanism 532b, along with their respective high voltage wires, i.e. the first high voltage wire 522a and second high voltage wire 522b, are free to move independently, i.e. are not constrained, so that any particulates, i.e. particulates 630 of FIG. 6B, that accumulate on the plurality of carbon bristles 628 are ejected from the plurality of carbon bristles 628 due to one or more of a vibratory force, an inertial force, and/or a fictional force. In various embodiments, the ejected particulates may then be captured in an adjacent air filter within the air handling system with which the smart air ionizer 510 is associated.

Figure 7:
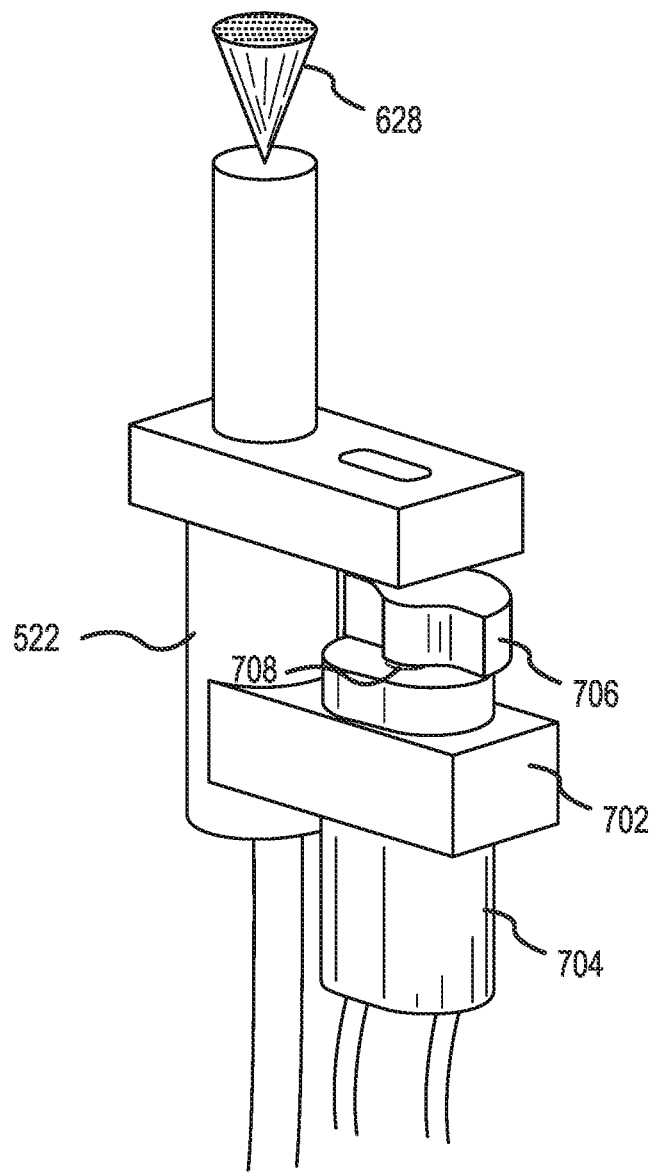
FIG. 7 illustrates an enlarged diagram of a cleaning mechanism coupled to and in physical contact with a high voltage wire, in accordance with an illustrative embodiments.

Referring now to FIG. 7, an enlarged diagram of a cleaning mechanism coupled to and in physical contact with a high voltage wire is illustrated, in accordance with illustrative embodiments. In various embodiments, the cleaning mechanism 532, such as the first cleaning mechanism 532a and the second cleaning mechanism 532b of FIG. 5, is coupled to and in physical contact with high voltage wire 522, such as the first high voltage wire 522a or the second high voltage wire 522b of FIG. 5, via coupler 702. In various embodiments, the cleaning mechanism 532 is a motor 704 with an offset (non-symmetric) mass 706 attached to a shaft 708 of the motor 704. In various embodiments, as the motor 704 rotates, the centripetal force of the offset mass 706 is asymmetric, resulting in a net centrifugal force, and this causes a displacement of the motor 704 and thus, the high voltage wire 522. In various embodiments, the displacement of the high voltage wire 522 via the displacement of the motor 704 causes one or more of a vibratory force, an inertial force, and/or a fictional force to be placed on the plurality of carbon bristles 628 and thereby an ejection of any accumulated particulates on the plurality of carbon bristles 628.

Figure 8:
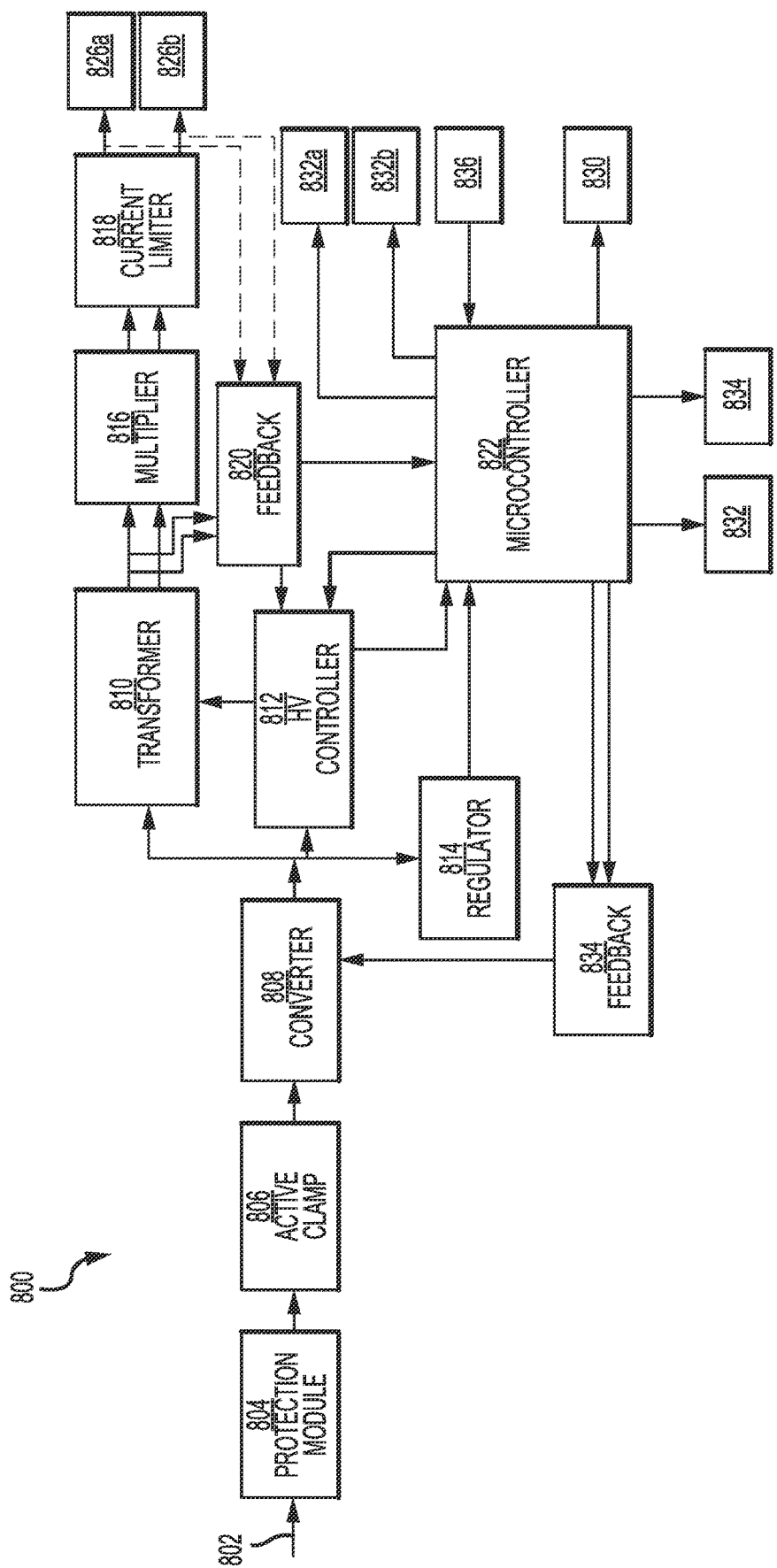
FIG. 8 illustrates a system diagram of a smart air ionizer, in accordance with various embodiments.

Referring now to FIG. 8, a diagram of system 800 of an air ionizer circuit is illustrated, in accordance with various embodiments. System 800 may be an example of air ionizer circuit 514 and high voltage circuit 516 described above with respect to FIG. 5. System 800 includes a power input 802, a protection module 804, an active clamp 806, and a converter 808, which may be collectively referred to as a power circuit. In various embodiments, power input 802 may provide 18 VDC to 32 VDC, and more specifically, may provide 28 VDC to system 800. In various embodiments, power input 802 may provide 110 VAC to 240 VAC, and more specifically, may provide 115 VAC to system 800. In various embodiments, system 800 may optionally include an AC-DC converter to convert AC voltage input to DC voltage. In various embodiments, protection module 804 may provide electrostatic discharge (ESD) and/or surge protection for system 800. In various embodiments, active clamp 806 may provide protection for the power supply (e.g., power input 802) against back electric and magnetic fields (EMF). In various embodiments, converter 808 may be a DC-DC voltage converter. In various embodiments, converter 808 may be a buck-boost converter to step-down DC voltage or step-up DC voltage.

System 800 further includes a transformer 810, a high voltage controller 812, a regulator 814, a multiplier 816, a current limiter 818, a feedback circuit 820, a controller 822, a feedback switch 834, a first electrode 826a, a second electrode 826b, first cleaning mechanism 832a, and the second cleaning mechanism 832b. In various embodiments, transformer 810 may be an isolation transformer driver that provides separation from power input 802 and high voltage controller 812 first and second electrodes 826a, 826b. In various embodiments, transformer 810 may receive a voltage from converter 808 to be provided to multiplier 816. In various embodiments, multiplier 816 may multiply, or step-up, the voltage provided by transformer 810 to a high voltage for use by first and second electrode 826a, 826b. Multiplier 816 provides the high voltage to current limiter 818 that the supplies the high voltage and limited current to first and second electrode 826a, 826b while maintaining the high voltage.

In various embodiments, the high voltage provided to first and second electrodes 826a, 826b may be about 2.5 KV to about 12.5 KV, and more specifically, about 5 KV to about 10 KV. In various embodiments, the current provided to first and second electrodes 826a, 826b may be about 100 µA to about 1 mA, and more specifically, about 250 µA to about 750 µA. By applying a high voltage with a limited current to first and second electrode 826a, 826b, little to no ozone is produced by first and second electrodes 826a, 826b during the air ionizing process. Producing little to no ozone provides increased safety for use in enclosed spaces (e.g., aircraft 100) and is an improvement over existing systems.

There is a first feedback path between current limiter 818 and feedback circuit 820 that provides the voltage and current output of current limiter 818 is provided to feedback circuit 820. In various embodiments, there may be a second feedback path between transformer 810 and feedback circuit 820 that provides the voltage and current output of transformer 810 to feedback circuit 820. Feedback circuit 820 provides the voltage and current output to high voltage controller 812 and controller 822. The feedback provided allows high voltage controller 812 and controller 822 to vary output voltage, output current, and ion count and provide improved performance of system 800.

High voltage controller 812 receives power from converter 808 and is configured to control the transformer 810 based on determined operation parameters (e.g., ion count) and feedback received from feedback circuit 820. In various embodiments, regulator 814 may receive power from converter 808 and provide a power supply to controller 822. Controller 822 may communicate with high voltage controller 812 to provide the determined operation parameters (e.g., ion count). In various embodiments, controller 822 may be configured to receive input and provide output for system 800. In various embodiments, controller 822 may send instructions to high voltage controller 812 to change operating parameters.

In various embodiments, controller 822 may be configured to, based on the determined operation parameters (e.g., ion count), turn the first cleaning mechanism 832a and the second cleaning mechanism 832b on or off in order to improve the ion count. In that regard, responsive to the ion count falling below a predetermined level, the controller 822 may turn on the first cleaning mechanism 832a and the second cleaning mechanism 832b in order to eject any particulates that may have accumulated on the plurality of carbon bristles through one or more of a vibratory force, an inertial force, and/or a fictional force.

System 800 further includes an input 836, an output 838, a first communication bus 840, and a second communication bus 842. In various embodiments, input 836 may be a keypad. In various embodiments, input 836 may be a button or a switch. In various embodiments, input 836 may be a touch screen interface. In various embodiments, input 836 may further include an ion probe for detecting the number of ions produced by first and second electrodes 826a, 826b. In various embodiments, output 838 may be a screen, an LED, or light, among others. In various embodiments, input 836 and output 838 may be combined in a touch screen. In various embodiments, first communication bus 840 and second communication bus 842 may be a serial peripheral interface (SPI) bus, a universal asynchronous receiver-transmitter (UART) bus, a controller area network (CAN) bus, or an ethernet connection, among others.

Controller 822 may include one or more processors configured to implement various logical operations in response to execution of instructions, for example, instructions stored on a non-transitory, tangible, computer-readable medium. The one or more processors can be a general-purpose processor, a microprocessor, a microcontroller, a digital signal processor (DSP), an application specific integrated circuit (ASIC), a field programmable gate array (FPGA) or other programmable logic device, discrete or transistor logic, discrete hardware components, or any combination thereof. Controller 822 may further include memory to store data, executable instructions, system program instructions, and/or controller instructions to implement the control logic of controller 822.

High voltage controller 812 may include one or more controllers configured to implement various logical operations in response to execution of instructions, for example, instructions stored on a non-transitory, tangible, computer-readable medium. The one or more controllers can be a voltage switching regulator, a pulse width modulation (PWM) controller, a PWM driver, an application specific integrated circuit (ASIC), discrete or transistor logic, discrete hardware components, or any combination thereof, among others. High voltage controller 812 may further include memory to store data, executable instructions, system program instructions, and/or controller instructions to implement the control logic of high voltage controller 812.

Figure 9:
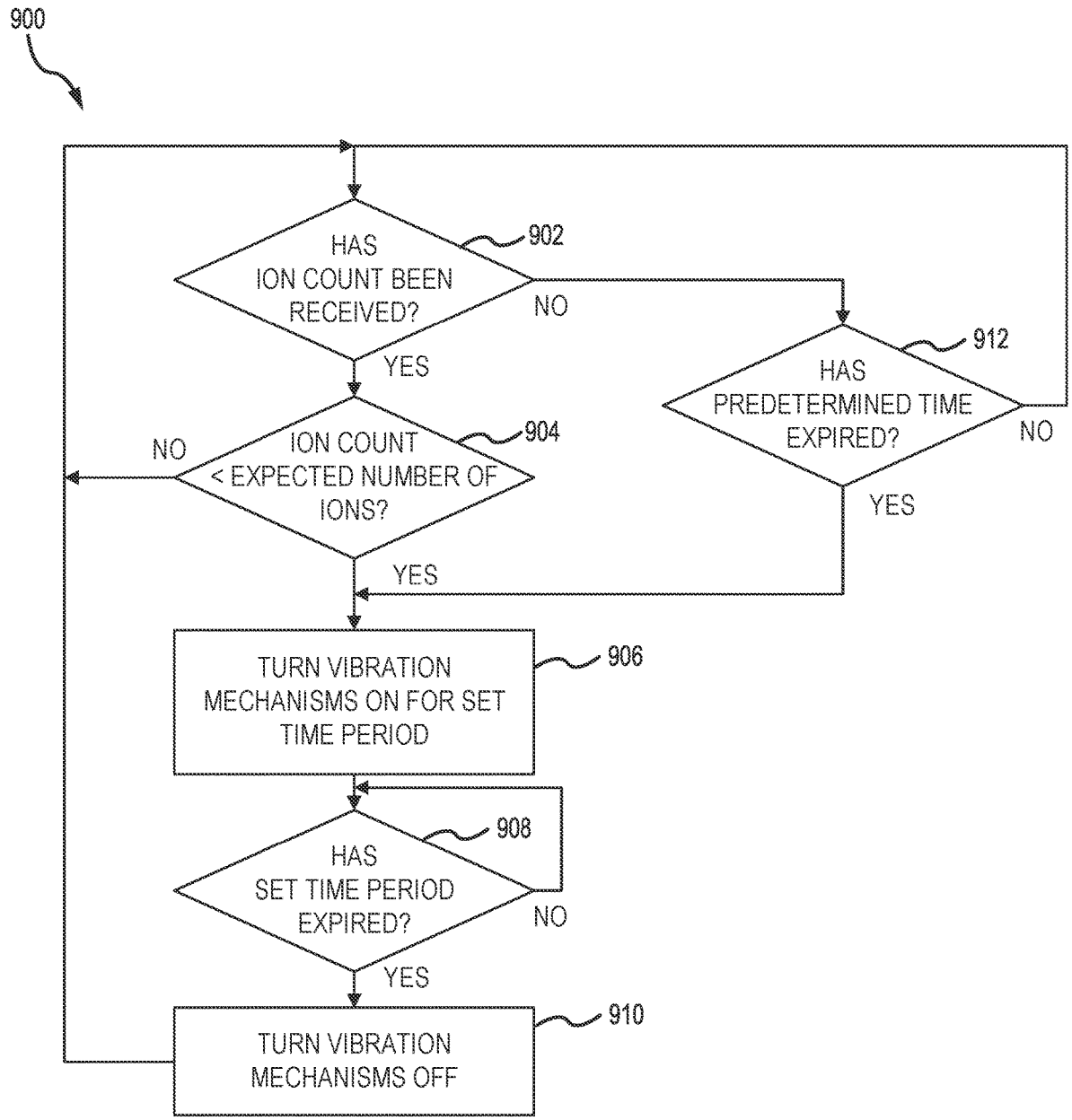
FIG. 9 illustrates a method for controlling an auto-cleaning mechanism of a smart air ionizer, in accordance with various embodiments

Referring now to FIG. 9, a method 900 for controlling an auto-cleaning mechanism of a smart air ionizer is illustrated, in accordance with various embodiments. In various embodiments, the smart air ionizer may be smart air ionizer 510 or system 800 described above with respect to FIGS. 5 and 8, respectively. In various embodiments, method 900 may be performed by air ionizer circuit 514 or controller 822 described above with respect to FIGS. 5 and 8.

At decision block 902, controller 822 determines whether an ion count has been received. In various embodiments, the ion count may be received from an ion probe connected to controller 822. In various embodiments, the ion count may be measured as a total number of ions or as a sample number of ions.

If at decision block 902 it is determined that an ion count has been received, then, at decision block 904, controller 822 determines whether the number of ions counted is less than an expected number of ions, an ion threshold. If at decision block 904 it is determined that the number of ions is less than the number of ions expected, at block 906, controller 822 sends a command to turn on the vibration mechanisms for a set time period, such as the first cleaning mechanism 532a and the second cleaning mechanism 532b of FIG. 5 or the first cleaning mechanism 832a and the second cleaning mechanism 832b of FIG. 8.

At decision block 908, controller 822 determines whether the set time period has expired. If at decision block 908 the set time period has not expired, the method 900 returns to decision block 908. If at decision block 908 the set time period has expired, controller 822 sends a command to turn off the vibration mechanisms.

Returning to decision block 904, if it is instead determined that the number of ions counted meets or exceeds the number of ions expected, method 900 returns to decision block 902. Method 900 then proceeds as described above.

Returning to decision block 902, if it is instead determined that an ion count has not been received, then, at decision block 912, controller 822 determines whether a predetermined time period has expired. If at decision block 912 the predetermined time period has not expired, the method 900 returns to decision block 902. If at decision block 912 the predetermined time period has expired, the method proceeds to decision block 908.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 5% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 5% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A cleaning mechanism for a smart air ionizer, comprising:
  an electrode configured with a plurality of carbon bristles exposed to an airflow and configured to ionize air in the airflow via the plurality of carbon bristles;
  a vibration mechanism;

a controller circuit coupled to the vibration mechanism, the controller circuit including a controller configured to operate the vibration mechanism to clean the plurality of carbon bristles; and an ion probe connected to the controller, wherein the controller is configured to receive a detected ion count from the ion probe and operate the vibration mechanism based on the detected ion count.

2. The smart air ionizer of claim 1, wherein the controller operates the vibration mechanism based on a predetermined ion threshold.

3. The smart air ionizer of claim 2, wherein the controller sends command to the vibration mechanism to clean the plurality of carbon bristles in response to at least one of the detected ion count failing to meet the predetermined ion threshold or the detected ion count failing to exceed the predetermined ion threshold.

4. The smart air ionizer of claim 1, wherein the vibration mechanism is coupled to the electrode.

5. The smart air ionizer of claim 1, wherein the vibration mechanism cleans the plurality of carbon bristles through vibrating the electrode.

6. The smart air ionizer of claim 1, wherein the vibration mechanism vibrates the electrode at a predetermined frequency.

7. The smart air ionizer of claim 1, wherein the vibration mechanism is at least one of an eccentric rotating mass (ERM) motor or a printed circuit board (PCB) motor.

8. The smart air ionizer of claim 1, wherein cleaning the plurality of carbon bristles ejects particulates that have accumulated on the plurality of carbon bristles.

9. A passenger service unit for use above an airline seat, comprising:
a body;
an air outlet mounted to the body;
an electrode mounted adjacent the air outlet, the electrode configured with a plurality of carbon bristles exposed to an airflow to ionize air in the airflow;
a vibration mechanism;
an air ionizer circuit connected to the electrode;
a processor coupled to the air ionizer circuit; and
a memory operatively coupled to the processor, the memory comprising instructions stored thereon that, when executed by the processor, cause the processor to:
receive a detected ion count from an ion probe;
determine whether the detected ion count meets or exceeds a predetermined ion threshold; and
responsive to at least one of the detected ion count failing to meet the predetermined ion threshold or the detected ion count failing to exceed the predetermined ion threshold, send a command to the vibration mechanism to clean the plurality of carbon bristles.

10. The passenger service unit of claim 9, wherein the vibration mechanism is coupled to the electrode.

11. The passenger service unit of claim 9, wherein the vibration mechanism cleans the plurality of carbon bristles through vibrating the electrode.

12. The passenger service unit of claim 9, wherein the vibration mechanism vibrates the electrode at a predetermined frequency.

13. The passenger service unit of claim 9, wherein the vibration mechanism is at least one of an eccentric rotating mass (ERM) motor or a printed circuit board (PCB) motor.

14. The passenger service unit of claim 9, wherein cleaning the plurality of carbon bristles ejects particulates that have accumulated on the plurality of carbon bristles.

15. A method for controlling an air ionizer, comprising:
receiving, by a processor, a detected ion count from a probe, the detected ion count being representative of ions produced by an electrode;
comparing, by the processor, the detected ion count to a predetermined ion threshold; and
responsive to the detected ion count being below the predetermined ion threshold, sending, by the processor, a command to a vibration mechanism to clean a plurality of carbon bristles coupled to the electrode.

16. The method of claim 15, wherein the vibration mechanism cleans the plurality of carbon bristles through vibrating the electrode.

17. The method of claim 15, wherein the vibration mechanism vibrates the electrode at a predetermined frequency.

18. The method of claim 15, wherein the vibration mechanism is at least one of an eccentric rotating mass (ERM) motor or a printed circuit board (PCB) motor.

19. The method of claim 15, wherein cleaning the plurality of carbon bristles ejects particulates that have accumulated on the plurality of carbon bristles.

* * * * *